(12) United States Patent
Algawi et al.

(10) Patent No.: US 11,173,285 B2
(45) Date of Patent: Nov. 16, 2021

(54) PRODUCING A GUIDEWIRE COMPRISING A POSITION SENSOR

(71) Applicant: Biosense Webster (Israel) Ltd., Yokneam (IL)

(72) Inventors: Yehuda Algawi, Binyamina (IL); Assaf Govari, Haifa (IL); Ilya Sitnitsky, Nahariya (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 378 days.

(21) Appl. No.: 16/022,562

(22) Filed: Jun. 28, 2018

(65) Prior Publication Data

US 2020/0001052 A1  Jan. 2, 2020

(51) Int. Cl.
*A61M 25/09* (2006.01)
*A61M 25/01* (2006.01)

(52) U.S. Cl.
CPC ........ *A61M 25/09* (2013.01); *A61M 25/0127* (2013.01); *A61M 2025/09083* (2013.01); *A61M 2025/09108* (2013.01); *A61M 2025/09133* (2013.01); *A61M 2210/065* (2013.01); *A61M 2210/0618* (2013.01); *A61M 2210/0662* (2013.01); *A61M 2210/12* (2013.01)

(58) Field of Classification Search
CPC .............. A61M 25/0127; A61M 25/09; A61M 2025/09083; A61M 2025/09108; A61M 2025/09133; A61M 2210/0618; A61M 2210/065; A61M 2210/0662; A61M 2210/12
See application file for complete search history.

(56) References Cited

U.S. PATENT DOCUMENTS

| | | | |
|---|---|---|---|
| 3,381,459 A | 5/1968 | Vawter | |
| 5,391,199 A | 2/1995 | Ben-Haim | |
| 5,517,812 A | 5/1996 | Simmons | |
| 5,517,989 A * | 5/1996 | Frisbie | A61B 5/0422 600/585 |
| 6,142,958 A * | 11/2000 | Hammarstrom | A61B 5/6851 600/486 |
| 6,239,724 B1 | 5/2001 | Doron et al. | |

(Continued)

FOREIGN PATENT DOCUMENTS

| | | |
|---|---|---|
| WO | WO9605768 | 2/1996 |
| WO | 2014043704 A1 * | 3/2014 |

(Continued)

OTHER PUBLICATIONS

European Search Report dated Dec. 12, 2019 from corresponding European Patent Application No. 19182801.1.

(Continued)

*Primary Examiner* — Carl J Arbes
(74) *Attorney, Agent, or Firm* — Frost Brown Todd LLC (57) ABSTRACT

A method for producing a guidewire, the method includes producing a position sensor by providing a shaft-section having a solid profile, which is sized and shaped to move in an anatomical material transportation system. A wire is wound around an axis of the shaft-section and first and second ends of the wire are coupled to respective first and second locations on an outer surface of the shaft-section. A guidewire-shaft is provided, and the position sensor is coupled to a distal end of the guidewire-shaft.

20 Claims, 4 Drawing Sheets

(56) References Cited

U.S. PATENT DOCUMENTS

| | | | |
|---|---|---|---|
| 6,332,089 B1 | 12/2001 | Acker et al. | |
| 6,484,118 B1 | 11/2002 | Govari | |
| 6,618,612 B1 | 9/2003 | Acker et al. | |
| 6,690,963 B2 | 2/2004 | Ben-Haim et al. | |
| 7,720,521 B2 | 5/2010 | Chang et al. | |
| 7,881,769 B2* | 2/2011 | Sobe | A61B 17/3207 |
| | | | 600/424 |
| 8,231,537 B2* | 7/2012 | Ahmed | A61B 5/02158 |
| | | | 600/485 |
| 8,579,825 B2* | 11/2013 | Tenerz | A61M 25/09 |
| | | | 600/488 |
| 9,095,685 B2* | 8/2015 | Sela | A61B 5/065 |
| 10,065,015 B2* | 9/2018 | Leeflang | A61M 25/0012 |
| 10,124,145 B2* | 11/2018 | Leeflang | A61M 25/0029 |
| 10,201,284 B2* | 2/2019 | McCaffrey | A61B 5/0215 |
| 10,646,122 B2* | 5/2020 | McCaffrey | A61B 5/02028 |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2011/0066029 A1 | 3/2011 | Lyu et al. | |
| 2012/0172761 A1 | 7/2012 | Meller et al. | |
| 2013/0169272 A1 | 7/2013 | Eichler et al. | |
| 2013/0296692 A1 | 11/2013 | Vanney et al. | |
| 2014/0159707 A1 | 6/2014 | Ashe | |
| 2014/0187893 A1 | 7/2014 | Clark et al. | |
| 2014/0323964 A1* | 10/2014 | Leeflang | A61M 25/0012 |
| | | | 604/95.04 |
| 2016/0276739 A1 | 9/2016 | Buesseler et al. | |
| 2017/0224237 A1 | 8/2017 | Basu et al. | |

FOREIGN PATENT DOCUMENTS

| | | |
|---|---|---|
| WO | 2017/024289 A1 * | 2/2017 |
| WO | WO 2017/017659 | 2/2017 |
| WO | WO 2018/042271 | 3/2018 |

OTHER PUBLICATIONS

European Exam Report dated Aug. 25, 2020 from corresponding European Patent Application No. 19182801.1.

* cited by examiner

PRODUCING A GUIDEWIRE COMPRISING A POSITION SENSOR

FIELD OF THE INVENTION

The present invention relates generally to invasive medical devices, and particularly to methods and systems for producing a position sensor of a guidewire.

BACKGROUND OF THE INVENTION

Guidewires comprising sensors may be used in various medical applications, such as in cardiology and sinuplasty.

For example, U.S. Patent Application Publication 2011/0066029, now abandoned, describes an insertable or implantable medical device that includes an elongated member having a proximal end, a distal end, at least one conductive coil near the distal end, and electrical conductors which carry current from the coil towards the proximal end. The coil surrounds or is surrounded by a flexible magnetic polymeric composite.

U.S. Patent Application Publication 2012/0172761, issued as U.S. Pat. No. 8,764,683 on Jul. 1, 2014, describes a guidewire for a medical device. The guidewire includes a core-wire having a proximal end portion and a distal end portion, an elongate shroud disposed about the core-wire, the shroud having a distal end, and a plug coupled with the distal end portion of the core-wire and the distal end of the shroud, the plug having a distal, non-traumatic tip portion, an interior between the core-wire and the shroud being configured to receive a sensor.

SUMMARY OF THE INVENTION

An embodiment of the present invention that is described herein provides a method for producing a guidewire, the method includes producing a position sensor by providing a shaft-section having a solid profile, which is sized and shaped to move in an anatomical material transportation system. A wire is wound around an axis of the shaft-section and first and second ends of the wire are coupled to respective first and second locations on an outer surface of the shaft-section. A guidewire-shaft is provided, and the position sensor is coupled to a distal end of the guidewire-shaft.

In some embodiments, the method includes producing the wire by cutting a wire-section from a continuous wire. In other embodiments, providing the shaft-section includes cutting the shaft-section from a continuous shaft. In yet other embodiments, the method includes moving the shaft-section by conducting at least one of: (i) moving the shaft-section along a direction parallel to the axis, and (ii) rotating the shaft-section about the axis.

In an embodiment, winding the wire includes a sequence of operations consisting of: (i) coupling the first end to the first location, (ii) moving the shaft-section, and (iii) coupling the second end to the second location. In another embodiment, the method includes, prior to winding the wire, coating the outer surface of the shaft-section with an electrically insulating biocompatible material.

In some embodiments, the electrically insulating biocompatible material includes polytetrafluoroethylene (PTFE). In other embodiments, the anatomical material transportation system includes an anatomical system selected from a list consisting of a vasculature system, an ear-nose-throat (ENT) system, and a neurological system.

There is additionally provided, in accordance with an embodiment of the present invention, a system for producing a guidewire, the system includes a sub-system for producing a position sensor and an integration assembly. The sub-system includes (i) a cutter, which is configured to produce a shaft-section, which is sized and shaped to move in an anatomical material transportation system, by cutting the shaft-section from a continuous shaft having a solid profile, and (ii) a wiring device, which is configured to wind a wire around an axis of the shaft-section, and to couple first and second ends of the wire to respective first and second locations on an outer surface of the shaft-section. The integration assembly is configured to couple the position sensor to a distal end of a guidewire-shaft of the guidewire.

The present invention will be more fully understood from the following detailed description of the embodiments thereof, taken together with the drawings in which:

DETAILED DESCRIPTION OF EMBODIMENTS

Overview

Embodiments of the present invention that are described hereinbelow provide improved methods and systems for producing guidewires comprising position sensors.

In some embodiments, a system for producing guidewires comprises a sub-system for producing a position sensor, and an integration assembly. In some embodiments, the sub-system comprises a cutter, which is configured to cut from a cylindrical shaft having a solid profile, a section, referred to herein as a shaft-section. The cutter is configured to cut the shaft, such that the shaft-section is sized and shaped to move in an anatomical material transportation system, e.g., the ear-nose-throat (ENT) system or the vasculature system.

In some embodiments, the sub-system further comprises a wiring device, which is configured to cut, from a continuous wire, a section, referred to herein as a wire-section, having first and second ends. The wiring device is further configured to wind the wire-section around a longitudinal axis of the shaft, and to couple the first and second ends of the wire-section to respective first and second predefined locations on an outer surface of the shaft-section. In the context of the present invention, the terms "longitudinal axis" and "axis" are used interchangeably and refer to the longitudinal axis, which is orthogonal to the circular cross-section of the shaft.

In some embodiments, the sub-system further comprises a motion assembly, configured to move the continuous shaft parallel to the axis, and simultaneously, to rotate the shaft about the axis. In some embodiments, the motion assembly is configured to move the shaft in a linear motion such that the cutter cuts the shaft-section from the continuous shaft at different locations. The motion assembly is further configured to move the shaft in a rotary motion so as to assist the wiring device in winding the wire-section around the axis of the shaft. In some embodiments, the integration assembly is configured to couple the position sensor to a distal end of a guidewire-shaft, which is a section of the guidewire.

The disclosed techniques enable improving the quality and functionality of guidewires, and reducing their production cost by producing high precision position sensors using fully automated high volume manufacturing (HVM) techniques.

System Description

Figure 1:
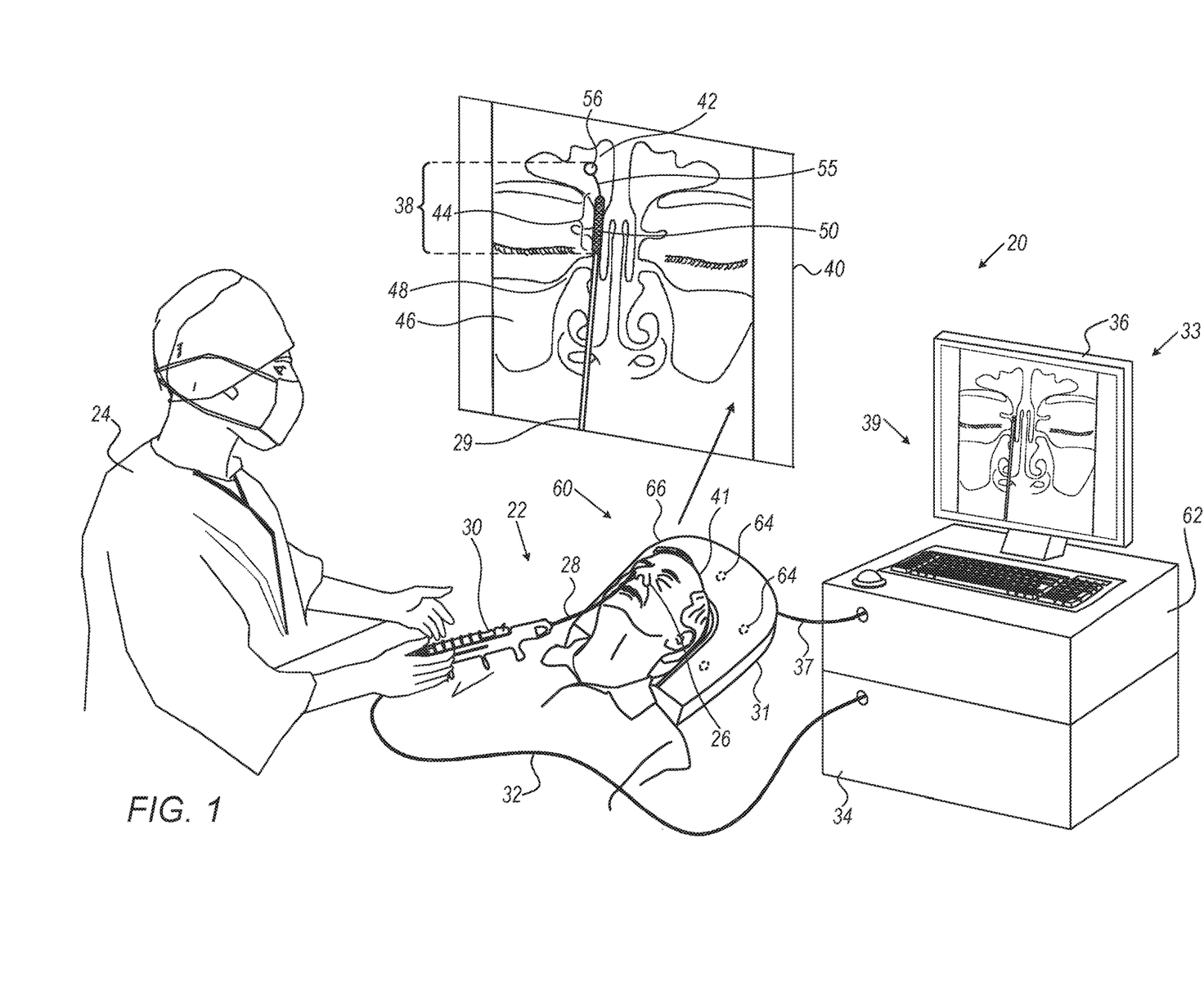
FIG. 1 is a schematic, pictorial illustration of a sinuplasty surgical system, in accordance with an embodiment of the present invention.

FIG. 1 is a schematic pictorial illustration of a sinuplasty procedure using a surgical system 20, in accordance with an embodiment of the present invention. System 20 comprises a catheter 28, which a physician 24 inserts into a nose 26 of a patient 22 so as to treat an ear-nose-throat (ENT) disease, such as infection in one or more sinuses of patient 22.

Reference is now made to an inset 40 that shows a frontal anatomical view of the ENT system of patient 22. The ENT system of patient 22 comprises a frontal sinus 42 and a maxillary sinus 46. Ostia 44 and 48 connect between cavities of the nose (not shown) and sinuses 42 and 46, respectively. Catheter 28 comprises a guidewire 29 having a distal end 38. In an embodiment, the tip of distal end 38 comprises a position sensor 56 attached at the end of a residual end section 55 of guidewire 29. Position sensor 56 may function as a single-axis sensor (SAS) or as a multi-axis sensor, e.g., a triple-axes sensor (TAS) as will be described in detail in FIG. 2 below.

Catheter 28 further comprises an inflatable balloon 50, which may be configured in two positions, e.g., an expanded (inflated) position and a collapsed position. When balloon 50 is in the collapsed position, the catheter can be navigated to the target location. The balloon is then inflated to the expanded position using a suitable fluid (e.g., a saline solution so as to anchor catheter 28 at the target location (e.g., ostium 44) in the ENT system of patient 22.

Catheter 28 further comprises a handle 30, which is located at the proximal end of catheter 28. Handle 30 is configured to control the navigation of guidewire 29 and the motion of balloon 50 along guidewire 29.

In some embodiments, system 20 further comprises a location pad 60 placed at a known position external to patient 22 lying on table 31, pad 60 comprises field-generators 64 fixed on a frame 66. In the exemplary configuration shown in FIG. 1, pad 60 comprises five field-generators 64, but may alternatively comprise any other suitable number of field-generators 64. Pad 60 further comprises a pillow (not shown) placed under a head 41 of patient 22, such that field-generators 64 are located at fixed, known positions external to head 41.

In some embodiments, system 20 comprises a console 33, which comprises a driver circuit 62 configured to drive, via a cable 37, field-generators 64 with suitable signals so as to generate magnetic fields in a predefined working volume in space around head 41. In some embodiments, console 33 comprises a processor 34, typically a general-purpose computer, with suitable front end and interface circuits for receiving, via a cable 32, signals from catheter 28. Console 33 further comprises input devices 39 and a display 36, which is configured to display data (e.g., images) received from processor 34 or inputs inserted by a user (e.g., physician 24). In an embodiment, the position of position sensor 56 is typically measured by magnetic position sensing of a catheter position tracking system comprised in system 20.

This method of position sensing is implemented in various medical applications, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, issued as U.S. Pat. No. 6,690,963 on Feb. 10, 2004; 2003/0120150 A1, now abandoned; and 2004/0068178 A1, issued as U.S. Pat. No. 7,729,742 on Jun. 1, 2010, whose disclosures are all incorporated herein by reference.

During the sinuplasty procedure, physician 24 navigates the tip of guidewire 29 into sinus 42. In some cases, e.g., when treating infection in the sinus, it is important for the physician to anchor the distal tip of the catheter, for example by inflating balloon 50 in ostium 44.

In an embodiment, balloon 50 may be 16 mm long and may have a diameter of 5 mm, such as sinuplasty balloon produced by Acclarent Inc. (catalog number RSP0516MFS), yet any other suitable balloon with other dimensions may be used in the disclosed techniques.

In some cases, ostium 44 or any other part of the ENT system might be blocked or narrowed for guidewire 29 to pass therethrough. In some embodiments, balloon 50 is configured to expand ostium 44 so that physician 24 will be able to navigate guidewire, e.g., to sinus 42.

After inserting distal end 38 into the ENT system, physician 24 navigates balloon 50 to ostium 44. Note that, typically, balloon 50 does not comprise a position sensor and is not otherwise imaged on display 36. To perform the treatment safely and efficiently, it is important to position balloon 50 accurately within ostium 44. For example, positioning balloon 50 in the nose cavity, short of ostium 44, may not allow the physician to anchor end section 55 within sinus 42, whereas positioning the balloon within sinus 42, deeper than ostium 44, may disturb the physician in treating the infection therein.

In the example of FIG. 1, balloon 50 is used for expanding ostium 44 and/or for anchoring end section 55 within sinus 42. In alternative embodiments, any other suitable device may be positioned using the disclosed techniques, instead of balloon 50. Such a device may comprise, for example, an alternative anchoring device for anchoring the end section or for any other diagnostic or treatment purpose. For example, a balloon may be used for treating cardiac arrhythmia at a pulmonary vein (PV) in a PV isolation procedure. In other applications, a drug dispensing device or a stent may be navigated to a specific location in a human organ, using the techniques described above.

In some embodiments, processor 34 is configured to assist physician 24 to position balloon 50 accurately within ostium 44. FIG. 1 shows only elements related to the disclosed techniques, for the sake of simplicity and clarity. System 20 typically comprises additional modules and elements that are not directly related to the disclosed techniques, and thus, intentionally omitted from FIG. 1 and from the corresponding description.

Processor 34 may be programmed in software to carry out the functions that are used by the system, and to store data in a memory (not shown) to be processed or otherwise used by the software. The software may be downloaded to the processor in electronic form, over a network, for example, or it may be provided on non-transitory tangible media, such as optical, magnetic or electronic memory media. Alternatively, some or all of the functions of processor 34 may be carried out by dedicated or programmable digital hardware components.

In some embodiments, catheter 28 and guidewire 29 may be used in medical procedures applied to various human anatomical systems, such as but not limited to the vasculature system, ENT system, and neurological system.

Sensor Coil Wounded Around a Shaft Having a Solid Profile

Figure 2:
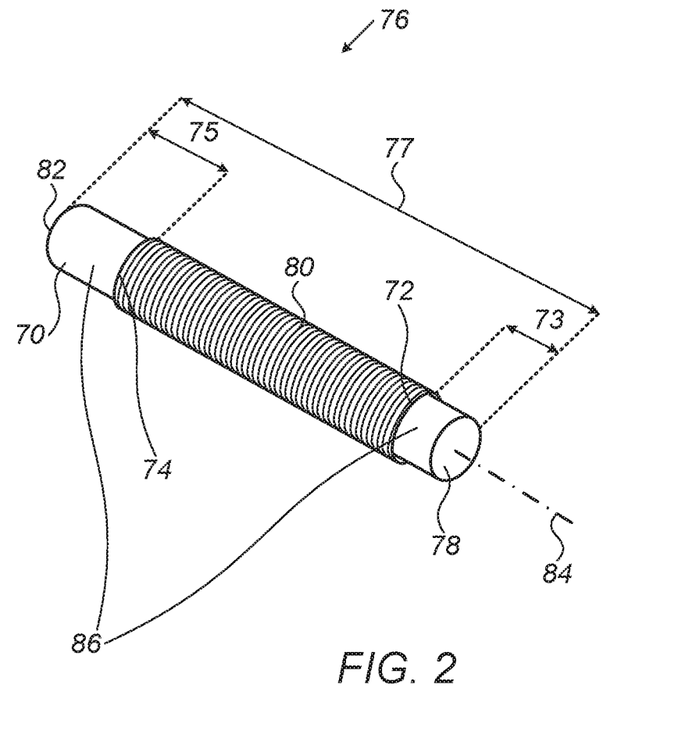
FIG. 2 is a schematic, pictorial illustration of a position sensor, in accordance with an embodiment of the present invention.

FIG. 2 is a schematic, pictorial illustration of a position sensor 76, in accordance with an embodiment of the present invention. Position sensor 76 may replace, for example, position sensor 56 of FIG. 1 above, and may function as a SAS or as any other type of position sensor.

In some embodiments, position sensor 76 comprises a shaft 70 sized and shaped to move in an anatomical material transportation system of patient 22, such as in the vasculature system or in the ENT system described in FIG. 1 above. In some embodiments, shaft 70 has a cylindrical-shaped solid profile having a circular cross-section. Shaft 70 is typically made from steel (e.g., molded steel or ferrite powder that provides high electrical conductivity) or from any suitable biocompatible material. In some embodiments, shaft 70 has a longitudinal axis 84, an outer surface 86, and a length 77 defined between a distal end 78 and a proximal end 82 of the shaft. In an embodiment, surface 86 of shaft 70 is coated with a suitable electrically insulating biocompatible material such as polytetrafluoroethylene (PTFE), known as Teflon™ or polycarbonate-based coating, which is electrically insulated and prevents slipping of an electrically conductive coil 80 (described in detail below) over shaft 70, or any other suitable coating. The PTFE coating may be carried out before receiving shaft 70, or during the production process of position sensor 56, as will be described in FIGS. 3 and 4 below.

In some embodiments, position sensor 76 comprises electrically conductive coil 80, made from a copper wire or from any other suitable electrically-conductive material. Coil 80 is wound around axis 84 and is coupled to the biocompatible material coating outer surface 86. In the example of FIG. 2, the distal and proximal ends of coil 80 are coupled (e.g., cemented, glued, soldered) to the biocompatible material at predefined coupling locations 72 and 74, respectively. Note that coupling location 72 is set at a predefined distance 73 from distal end 78, and coupling location 74 is set at a predefined distance 75 from proximal end 82.

In some embodiments, position sensor 76 is coupled, e.g., at proximal end 82, to a guidewire as shown in FIG. 1 above. Following the example of FIG. 1, position sensor 76 may be coupled (instead of sensor 56) to end section 55, also referred to herein as a guidewire-shaft, which is a section of guidewire 29. Note that shaft 70 serves as a core element of position sensor 76, whereas coil 80, which is electrically insulated from shaft 70, is wound around axis 84 of shaft 70.

The configuration of position sensor 76 is provided by way of example and any other suitable configurations can also be used. For example, shaft 70 may have a non-circular cross-section shape and may have any suitable interior structure, such as having a partially or fully hollowed profile. Furthermore, position sensor 76 may comprise multiple coils (e.g., three coils) arranged in any suitable configuration so as to form a multi-axes sensor (e.g., a TAS).

Producing a Position Sensor of a Guidewire

Figure 3:
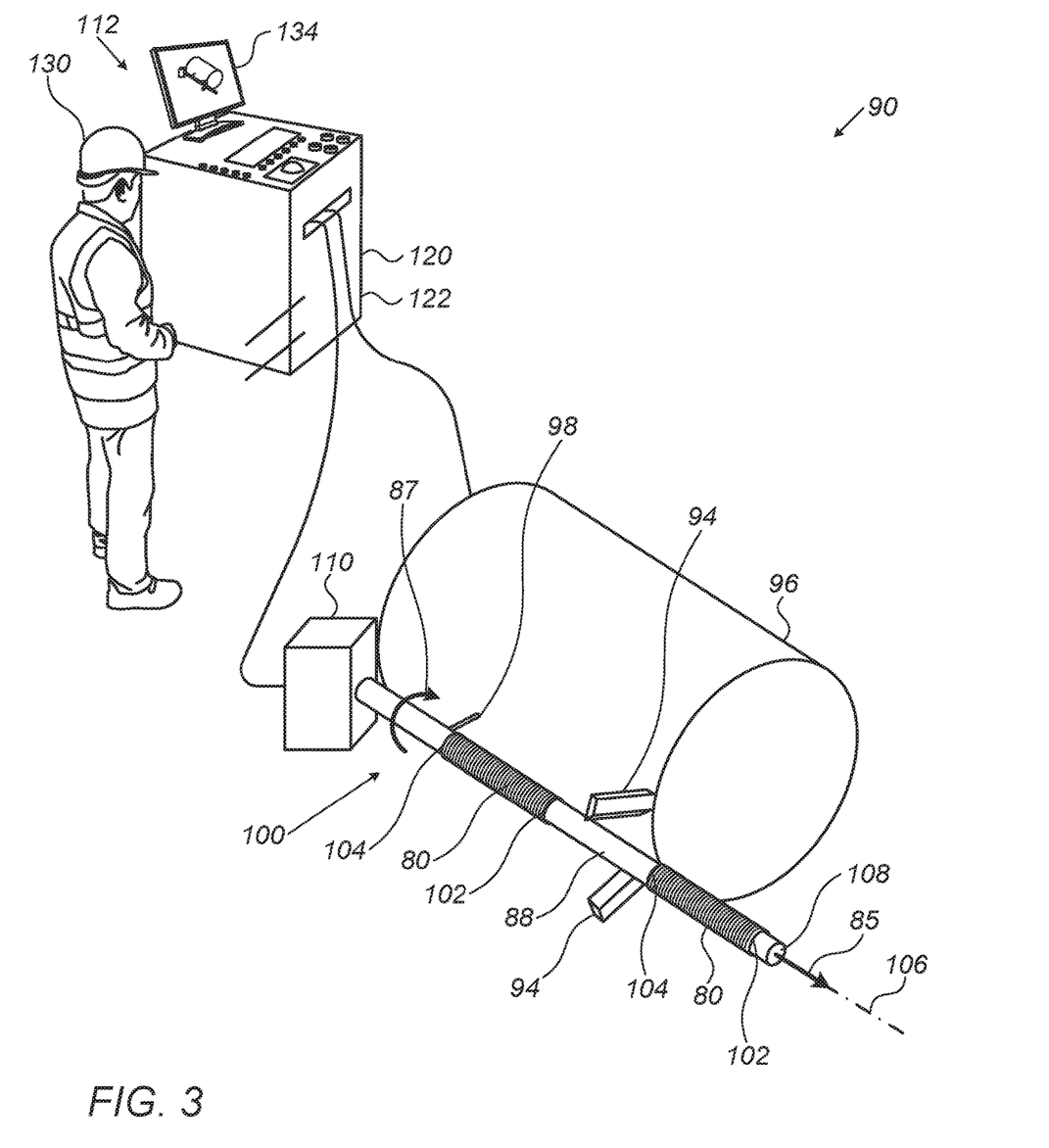
FIG. 3 is a schematic, pictorial illustration of a system for producing a position sensor, in accordance with an embodiment of the present invention.

FIG. 3 is a schematic, pictorial illustration of a system 90 for producing position sensor 76, in accordance with an embodiment of the present invention. In some embodiments, system 90 functions as a sub-system of a system for producing guidewire 29 comprising the position sensor, as will be described in detail below.

In some embodiments, system 90 comprises a drum-shaped assembly 96, which contains a continuous copper wire (not shown) that is typically long enough for producing multiple coils. In some embodiments, system 90 comprises a motion assembly 110 configured to move a continuous shaft 100 in a linear motion and in a rotary motion. In some embodiments, motion assembly 110 may comprise one or more linear and rotary motors and motion control capabilities such motion controllers (not shown) and encoders that provide position and/or velocity feedback to the motion controller. In other embodiments, motion assembly 110 may comprise any other suitable configuration that enables a controlled motion of shaft 100.

In the context of the present invention, with reference to a given longitudinal axis, the term "linear motion" refers to a straight motion along or in parallel to the longitudinal axis, and the term "rotary motion" refers to a circular motion about the longitudinal axis. In some embodiments, the linear and rotational motions are controlled to have respective motion speeds.

In some embodiments, the linear motion is carried out using a linear-motion motor in a direction indicated by an arrow 85, parallel to a longitudinal axis 106 of shaft 100. The rotary motion is indicated by an arrow 87 and is carried out using one or more rotary motors configured to rotate shaft 100 about axis 106 (clockwise and/or counterclockwise). In some embodiments, motion assembly 110 is configured to carry out the linear and rotary motion simultaneously. Alternatively, the linear and circular motions are divided into multiple motion steps that are carried out sequentially, using any suitable sequence.

In some embodiments, system 90 comprises one or more cameras (not shown) configured to acquire multiple images of system 90 and shaft 100, so as to control the operation of system 90 as will be described below. The multiple images may be formatted as a video sequence using any suitable video encoding protocol.

In some embodiments, system 90 comprises a control console 112, which is configured to receive the multiple images from the one or more cameras, and to control multiple assemblies of system 90, such as motion assembly 110, and assembly 96 based on the multiple images.

In some embodiments, console 112 comprises a processor 120, typically a general-purpose computer, with suitable front end and interface circuits for controlling assemblies 96 and 110, and for receiving signals therefrom. In some embodiments, processor 120 may be programmed in software to carry out the functions that are used by system 90, and the processor stores data for the software in a memory 122. The software may be downloaded to processor 120 in electronic form, over a network, for example, or it may be provided on non-transitory tangible media, such as optical, magnetic or electronic memory media.

In some embodiments, console 112 comprises a display 134, which is configured to display data and images received from processor 120, and/or information that is provided by an operator 130, using input devices (not shown) of console 112.

In some embodiments, assembly 96 comprises a cutter 94 configured to cut sections, referred to herein as shaft-sections, from shaft 100 at predefined locations or lengths, e.g., predefined locations 108 and 88. Note that cutter 94 is controlled by processor 120, such that the distance between locations 108 and 88 is substantially similar to length 77 of shaft 70 described in FIG. 2 above. In some embodiments, locations 88 and 108 may be marked on the outer surface of shaft 100, so that at least one of the cameras may acquire and send an image of the marked location to processor 120. In other embodiments, cutter 94 may be controlled by another controller (not shown), such as a motion controller of motion assembly 110. In these embodiments, the motion controller may signal cutter 94 to cut the shaft-section based on inputs from the encoders of assembly 110, e.g., using a suitable command. In these embodiments, the cameras may be omitted from the configuration of system 90 in which case there is no need to mark locations 88 and 108 on shaft 100.

In some embodiments, processor 120 may receive, e.g., from the camera or from the motion controller, a signal indicating that location 88 is aligned with cutter 94 and may signal cutter 94 to cut shaft 100 at location 88. Processor 120 is further configured to pause the motion of shaft 100 during the cutting operation, and to resume the motion after cutter 94 completes the cutting operation of shaft 100.

In some embodiments, system 90 may comprise a coating device (not shown) configured to coat shaft 100 with one or more layers of PTFE. The coating device may be integrated into assembly 96, or a module of system 90, which is connected to and controlled by console 112. In alternative embodiments, shaft 100 may be coated before being inserted into system 90.

In some embodiments, assembly 96 comprises a wiring device 98 configured to cut sections of the continuous wire, referred to herein as wire-sections, and to wind each wire-section around an outer surface of a respective shaft-section cut from shaft 100. Wiring device 98 is further configured to couple the ends of the wire-section to shaft 100 at coupling locations 102 and 104, corresponding to coupling locations 72 and 74 of shaft 70 depicted in FIG. 2 above. In some embodiments, wiring device 98 may couple the ends to the outer surface of shaft 100 by dispensing a suitable biocompatible glue, or by soldering, or using any other suitable coupling technique.

In these embodiments, processor 120 is configured to receive from motion assembly 110 and/or from the cameras, signals indicative of the position of wiring device 98 relative to locations 102 and 104, and based on the received signals, to activate and deactivate the operations of wiring device 98 as described above.

For example, after coupling the first end of coil 80 at location 72, processor 120 signals motion assembly to move shaft 100 in the linear and rotary motions marked by arrows 85 and 87, so as to wind the continuous wire around shaft 100. When location 104 is aligned with wiring device 98, processor 120 signals motion assembly 110 to stop moving shaft 100 and further signals wiring device 98 to cut the continuous wire so as to form coil 80 and to couple, at location 104, the respective end of coil 80 to the outer surface of shaft 100. In an embodiment, processor 120 may receive a signal (e.g., from the camera) indicating that the coupling operation at location 104 has been completed, and subsequently, may signal motion assembly 110 to resume the linear (and optionally the rotary) motion of shaft 100 as described above.

In an embodiment, the rotary motion may be applied only when system 90 winds the wire around shaft 100. In an alternative embodiment, the rotary motion may be also used to assist cutter 94 in cutting shaft 100.

In some embodiments, system 90 may comprise an integration assembly (not shown), which is configured to couple position sensor 76 to end section 55 of guidewire 29.

This particular configuration of system 90 is shown by way of example, in order to illustrate certain problems that are addressed by embodiments of the present invention and to demonstrate the application of these embodiments in enhancing the performance of such a system. Embodiments of the present invention, however, are by no means limited to this specific sort of example system, and the principles described herein may be applied similarly to other sorts of production systems. For example, shaft 100 may be held in a static position and system 90 may be moved relative to shaft 100. Alternatively, system 90 may apply any other suitable technique to enable relative motion between shaft 100 and the assemblies of system 90 descried above.

Figure 4:
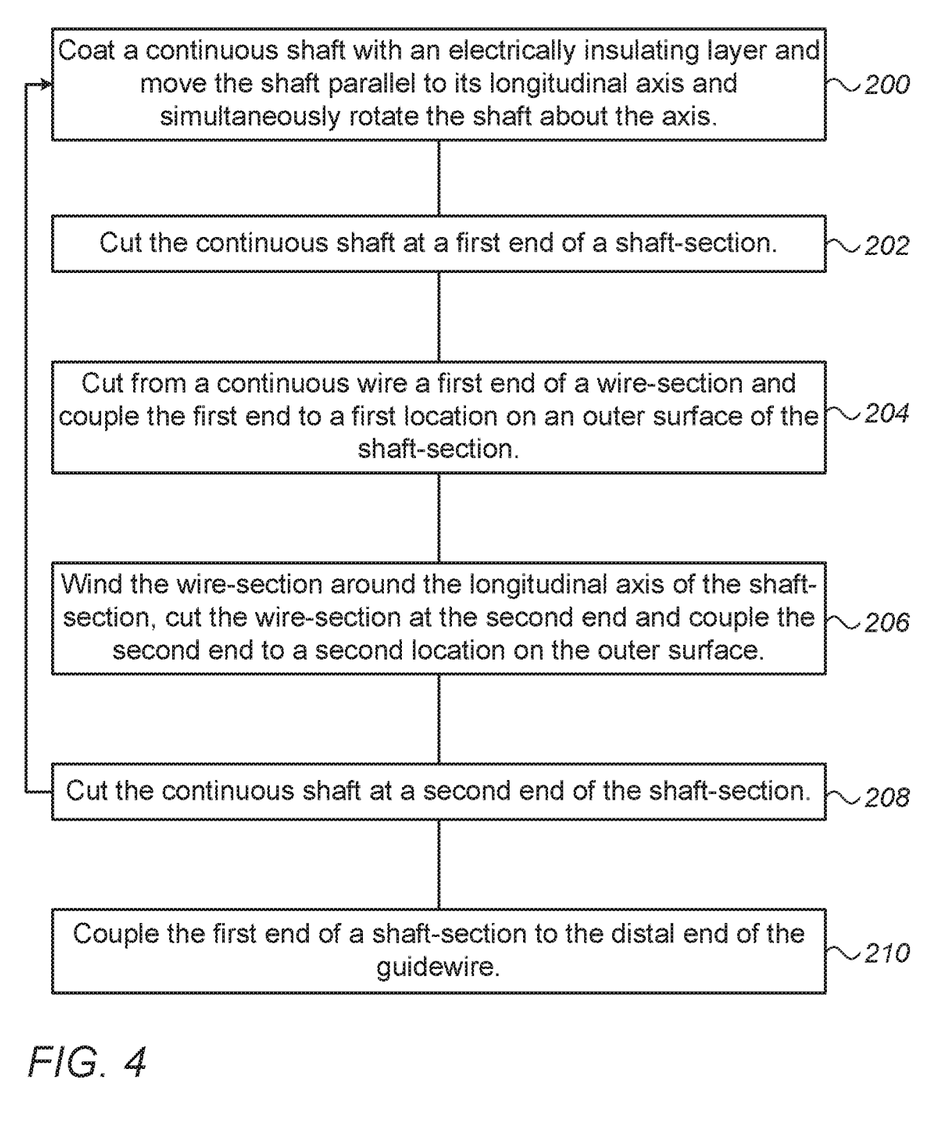
FIG. 4 is a flow chart that schematically illustrates a method for producing a guidewire having a position sensor, in accordance with an embodiment of the present invention.

FIG. 4 is a flow chart that schematically illustrates a method for producing guidewire 29 having position sensor 76, in accordance with an embodiment of the present invention. The method begins with coating shaft 100 with PTFE, or any other suitable biocompatible electrically insulating material. Note that the coating of shaft 100 may be carried out by system 90 during the production of position sensor 76, or by any other suitable system prior to inserting shaft 100 into system 90. In case shaft 100 is pre-coated, the method may begin with moving shaft 100 parallel to its longitudinal axis 106 and simultaneously rotating shaft 100 about axis 106, at a shaft moving step 200. As described above, the linear and rotary movements may be carried out simultaneously or in steps using any other suitable sequence. As described in FIG. 3 above, shaft moving step 200 may further comprise coating shaft 100 with PTFE in case the coating is carried out by system 90. The coating may be carried out by moving shaft 100 and winding PTFE around the outer surface of shaft 100, or using any other suitable coating technique.

At a first shaft-cutting step 202, cutter 94 cuts shaft 100 at predefined location 108. In an embodiment, before cutting shaft 100, processor 120 may signal motion assembly 110 to stop moving shaft 100, and after concluding the cut at location 108, to resume the linear and rotary motion of the shaft. In an alternative embodiment, the cut of shaft 100 may be carried out without pausing the movement of shaft 100. For example, the rotary motion may assist cutter 94 in cutting shaft 100, whereas the linear motion may be paused during shaft-cutting step 202.

At a wire-end coupling step 204, wiring device 98 cuts from the continuous wire, a first end of the wire-section, and couples the first end to coupling location 102. In some embodiments, processor 120 may command motion assembly 110 to stop moving shaft 100 so as to enable coupling the end of the wire to coupling location 102. After coupling the end of the wire to location 102, processor 120 may signal motion assembly 110 to resume the linear and rotary motion of shaft 100.

At a winding step 206, motion assembly 110 moves shaft 100 in parallel to axis 106, and simultaneously rotates shaft 100 about axis 106. Concurrently, wiring device 98 winds the wire-section around the outer surface of shaft 100. Subsequently, wiring device 98 cuts the wire-section at the second end and couples the second end of the wire-section to coupling location 104 so as to complete the winding of coil 80 around the shaft. Note that processor 120 may signal motion assembly 110 to stop moving shaft 100 so as to enable the coupling of the second end of the wire-section to coupling location 104, and after concluding the coupling, to resume the linear and rotary motion of shaft 100.

At a second shaft-cutting step 208, cutter 94 cuts shaft 100 at predefined location 88, thereby forming the shaft-section, which is substantially identical to shaft 70 of FIG. 2 above.

As depicted in step 202 above, processor 120 may signal motion assembly 110 to stop moving shaft 100 so as to carry out step 208.

Shaft-cutting step 208 concludes the formation of one position sensor 76. The method may loop back to moving step 200 so as to produce a second position sensor 76. Note that steps 200-208 are designed to produce a single position sensor. The method of FIG. 4 enables high volume manufacturing (HVM) of position sensors at a high precision.

At a section coupling step 210 that terminates the method, the first end of the shaft-section (e.g., proximal end 82 of position sensor 76) is coupled to the distal end of guidewire 29, so as to complete the formation of the guidewire having position sensor 76 coupled thereto. It will be understood that in alternative embodiments, distal end 78 of position sensor 76 may be coupled to the distal end of guidewire 29. Section coupling step 210 may be carried out in system 90, or alternatively, using a separate integration assembly (not shown) configured to carry out coupling step 210.

In other embodiments, the method may be limited to the formation of position sensor 76, and therefore may terminate after concluding shaft-cutting step 208. In these embodiments, the coupling of position sensor 76 to guidewire 29 may be carried out using another method as described, for example, at coupling step 210, or using any other suitable coupling technique.

Although the embodiments described herein mainly address a single axis position sensor coupled to a guidewire, the methods and systems described herein can also be used in other applications, such as in applications that require three-dimensional navigation, in which a TAS may be applied instead of or in addition to a SAS as described above.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system for producing a position sensor of a guidewire, the system comprising:
   (a) a wiring device configured to wind a single continuous wire around an outer surface of a continuous shaft having a solid profile, cut the single continuous wire to form a wire section having first and second ends, and couple the first and second ends of the wire-section to respective first and second locations on the outer surface of the continuous shaft; and
   (b) a cutter operatively associated with and positioned downstream of the wiring device, wherein the cutter is configured to cut the continuous shaft to form a shaft-section of the position sensor after the wire section is attached using the wiring device.

2. The system according to claim 1, and comprising a motion assembly, which is configured to move the shaft-section by conducting at least one of:
   (i) moving the shaft-section along a direction parallel to an axis defined by the shaft-section, and
   (ii) rotating the shaft-section about the axis.

3. The system according to claim 2, wherein the wiring device and the motion assembly are configured to wind the single continuous wire using a sequence of operations consisting of:
   (i) applying the wiring device, which is configured to couple the first end of the single continuous wire to the first location,
   (ii) applying the motion assembly, which is configured moving the shaft-section, and
   (iii) applying the wiring device, which is configured to couple the second end of the single continuous wire to the second location.

4. The system according to claim 1, and comprising a coating device operatively associated with and positioned upstream of the wiring device, wherein the coating device is configured to coat the outer surface with an electrically insulating biocompatible material.

5. The system according to claim 4, wherein the electrically insulating biocompatible material comprises polytetrafluoroethylene (PTFE).

6. The system according to claim 1, wherein the position sensor is sized and shaped to move in an anatomical material transportation system, wherein the anatomical material transportation system comprises an anatomical system selected from a list consisting of a vasculature system, an ear-nose-throat (ENT) system, and a neurological system.

7. The system according to claim 1, further comprising:
   (a) a camera configured to produce images; and
   (b) a controller configured to receive the images from the camera and control the system based on the images.

8. The system according to claim 7, wherein the controller further comprises:
   (a) a processor configured to receive the images from the camera; and
   (b) a display configured to display the images received from processor from the camera.

9. The system according to claim 8, wherein the processor is configured to pause motion of the continuous shaft while the cutter cuts the shaft-section and to resume the motion after the cutter completes the cutting of the shaft-section.

10. The system according to claim 7, further comprising a motion assembly operatively associated with the continuous shaft, wherein the motion assembly is configured to move the continuous shaft along an axis defined by the continuous shaft and rotate the continuous shaft as the single continuous wire is wrapped around the axis of the continuous shaft, wherein the controller is configured to receive the images from the camera and control the system based on the images.

11. A system for producing a position sensor of a guidewire, the system comprising:
   (a) a wiring device configured to wind a wire around an outer surface of a continuous shaft having a solid profile, cut the single continuous wire to form a wire section having first and second ends, and couple the first and second ends of the wire-section to respective first and second locations on the outer surface of the continuous shaft;
   (b) a cutter operatively associated with and positioned downstream of the wiring device, wherein the cutter is configured to cut the continuous shaft to form a shaft-section of the position sensor after the wire section is attached using the wiring device; and (c) a motion assembly operatively associated with the continuous shaft, wherein the motion assembly is configured to simultaneously move the continuous shaft along the longitudinal axis and rotate the continuous shaft as the wire is wrapped around the axis of the shaft-section.

12. The system according to claim 11, further comprises a second cutter configured to produce the shaft-section of the position sensor by cutting the shaft-section from the continuous shaft having the solid profile.

13. The system according to claim 11, further comprising:
(a) a camera configured to produce images; and
(b) a controller configured to receive the images from the camera and control the system based on the images.

14. A system for producing a position sensor of a guidewire, the system comprising:
(a) a wiring device configured to wind a wire around an outer surface of a continuous shaft having a solid profile, cut the single continuous wire to form a wire section having first and second ends, and couple the first and second ends of the wire-section to respective first and second locations on the outer surface of the continuous shaft;
(b) a cutter operatively associated with and positioned downstream of the wiring device, wherein the cutter is configured to cut the continuous shaft to form a shaft-section of the position sensor after the wire section is attached using the wiring device;
(c) a camera configured to produce images; and
(d) a controller configured to receive the images from the camera and control the system, including the wiring device and the cutter, based on the images.

15. The system according to claim 14, wherein the controller further comprises:
(a) a processor configured to receive the images from the camera; and
(b) a display configured to display the images received from the processor which received the images from the camera.

16. The system according to claim 15, wherein the processor is configured to pause motion of continuous shaft while the cutter cuts the shaft-section from the continuous shaft and to resume the motion after the cutter completes the cutting of the shaft-section from the continuous shaft.

17. The system according to claim 14, further comprising a motion assembly operatively associated with the continuous shaft, wherein the motion assembly is configured to move the continuous shaft along an axis defined by the continuous shaft and rotate the continuous shaft as the wire is around the axis of the shaft-section, wherein the controller is configured to receive the images from the camera and control the system based on the images.

18. The system according to claim 14, and further comprising a coating device operatively associated with and positioned upstream of the wiring device, wherein the coating device is configured to coat the outer surface with an electrically insulating biocompatible material.

19. The system according to claim 14, wherein the position sensor is sized and shaped to move in an anatomical material transportation system, wherein the anatomical material transportation system comprises an anatomical system selected from a list consisting of a vasculature system, an ear-nose-throat (ENT) system, and a neurological system.

20. The system according to claim 14, further comprises a second cutter configured to produce the shaft-section of the position sensor by cutting the shaft-section from the continuous shaft having the solid profile.

\* \* \* \* \*